US00PP24773P3

(12) United States Plant Patent
Dobres

(10) Patent No.: US PP24,773 P3
(45) Date of Patent: Aug. 19, 2014

(54) SHRUB ROSE PLANT NAMED 'NOVAROSPOP'

(50) Latin Name: *Rosa hybrida*
Varietal Denomination: Novarospop

(75) Inventor: Michael S. Dobres, Philadelphia, PA (US)

(73) Assignee: CP Delaware, Inc., Wilmington, DE (US)

( * ) Notice: Subject to any disclaimer, the term of this patent is extended or adjusted under 35 U.S.C. 154(b) by 45 days.

(21) Appl. No.: 13/507,960

(22) Filed: Aug. 9, 2012

(65) Prior Publication Data

US 2014/0047586 P1 Feb. 13, 2014

(51) Int. Cl.
*A01H 5/00* (2006.01)

(52) U.S. Cl.
USPC ..... Plt./104

(58) Field of Classification Search
USPC ..... Plt./104, 103
See application file for complete search history.

*Primary Examiner* — Kent L Bell
(74) *Attorney, Agent, or Firm* — Buchanan, Ingersoll & Rooney, PC

(57) ABSTRACT

A new and distinct shrub rose plant is provided that abundantly and substantially continuously forms in clusters attractive double cup-shaped blossoms that initially are yellow and change to cream-white with maturity. The plant exhibits vigorous vegetation and a bushy and rounded growth habit. The foliage is dark green with a glossy upper surface. The blossoms commonly display a very light sweet scent. Good disease resistance is displayed, particularly with respect to Black Spot, Powdery Mildew, and Rust, during observations to date. The plant is well suited for growing as attractive ornamentation in the landscape. It grows well as a ground cover, in mass plantings, and when present in a container.

2 Drawing Sheets

Botanical/commercial classification: *Rosa hybrida*/Shrub Rose Plant.

Varietal denomination: cv. Novarospop.

SUMMARY OF THE INVENTION

The new variety of *Rosa hybrida* shrub rose plant of the present invention was derived from the 'Meiggili' *Rosa hybrida* variety (U.S. Plant Pat. No. 18,542) through the use of mutagenesis followed by selection. More specifically, during January 2007 tissue cultured shoots of the 'Meiggili' variety were subjected to gamma radiation to form a population of plants which included various mutations. The resulting plants were rooted and transplanted during May 2007. Such plants thereafter were carefully studied and evaluated. A single invention was selected in view of its distinctive phenotype. Had this plant not been selected and preserved it would have been lost to mankind.

It was found that the new shrub rose plant of the present invention possesses the following combination of characteristics:

(a) abundantly and substantially continuously forms in clusters attractive double cup-shaped blossoms that initially are yellow and change to cream-white with maturity,
(b) exhibits good petal drop as the blossoms fully mature,
(c) exhibits a bushy and rounded growth habit,
(d) forms vigorous vegetation,
(e) forms attractive dark green foliage having a glossy upper surface that contrasts well with the light blossom coloration,
(f) exhibits good resistance to disease, and
(g) is well suited for providing attractive ornamentation in the landscape.

A new shrub rose variety is provided having attractive yellow changing to creamy-white at maturity blossoms combined with substantially continuous blooming and good disease resistance.

The new variety well meets the needs of the horticultural industry. It can be grown to advantage as ornamentation in parks, gardens, public areas, and in residential settings individually or as a ground cover or a mass planting or when grown in containers.

The new variety of the present invention can be readily distinguished from its ancestors and other previously available shrub rose varieties. More specifically, the 'Meiggili' parent variety displays blossoms that are bright peach in coloration.

As reported U.S. Plant Pat. No. 18,542, the parentage of the 'Meiggili' variety is as follows:

('Ruimired'×'Paul Crampel')×('Korimro'×'Lady Gay').

The 'Ruimired' variety is described in U.S. Plant Pat. No. 5,770, and the other ancestors are non-patented in the United States. Each ancestor forms blossoms of different coloration to that of the new variety. For instance, the 'Ruimired' variety forms dark red blossoms having no fragrance, the 'Paul Crampel' variety forms deep orange-scarlet blossoms, the 'Korimro' variety forms light pink blossoms, and the 'Lady Gay' variety forms dissimilar orange-pink blossoms that tend to appear only once per season.

Additionally, the new variety can be readily distinguished from other similar rose varieties, such as the 'Meilmera' variety (U.S. Plant Pat. No. 10,002) and the 'Meidarin' variety (U.S. Plant Pat. No. 13,291). The 'Meilmera' variety displays white blossoms, and the 'Meidrain' variety displays vibrant orange blossoms.

BRIEF DESCRIPTION OF THE PHOTOGRAPHS

The accompanying photographs show, as nearly true as it is reasonably possible to make the same in color illustrations of this character, the new variety of the present invention. The illustrated rose plant of the new variety was approximately one year of age and was observed during July 2012 while growing in a container outdoors on its own rootings near West Grove, Pa., U.S.A.

DETAILED BOTANICAL DESCRIPTION

Figure 1:
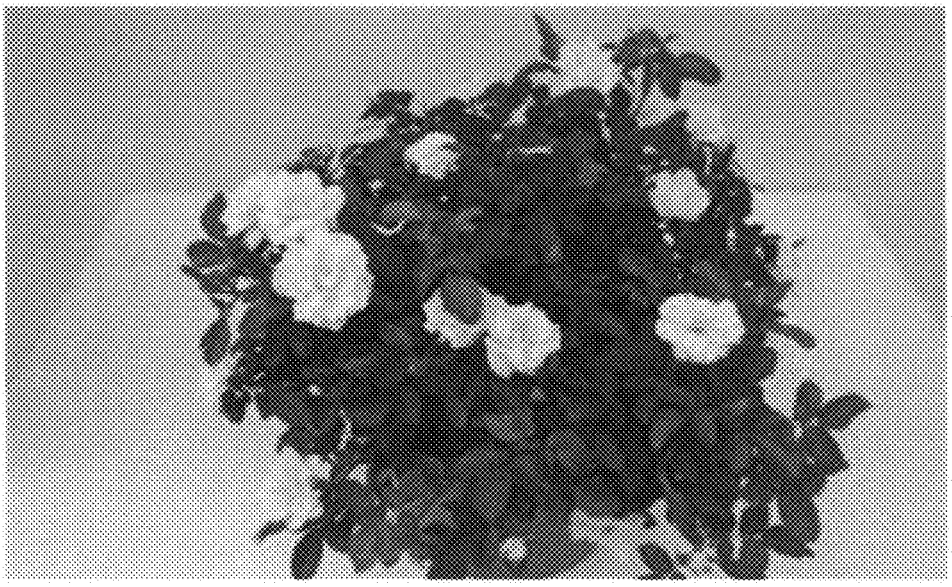
FIG. 1 illustrates the bushy rounded growth habit of a flowering plant.
Figure 2:
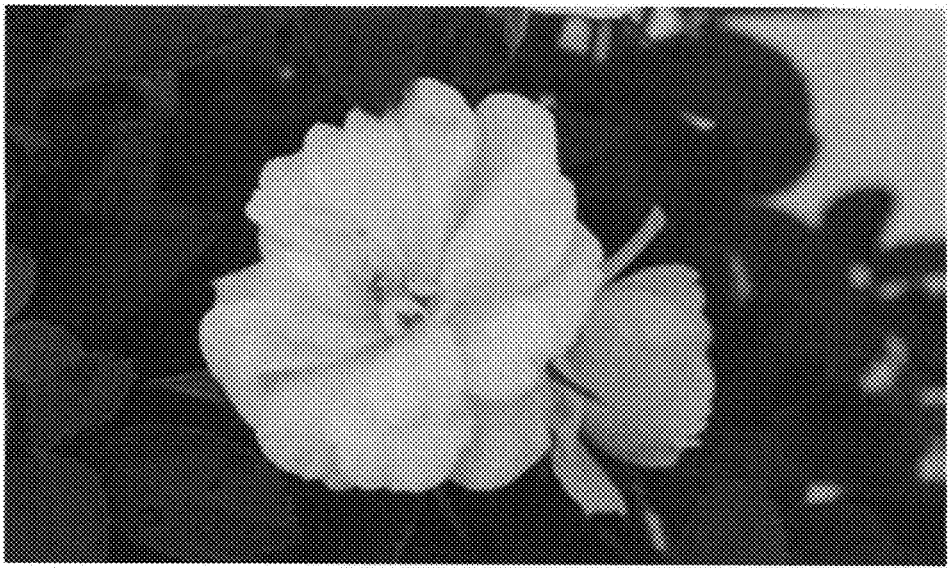
FIG. 2 illustrates a closer view of the yellow inflorescence and dark green foliage. The blossom on the left is in a more mature state and accordingly has lightened in coloration.

The chart used in the identification of colors is that of The Royal Horticultural Society (R.H.S. Colour Chart—1995 or equivalent), London, England. The description is based on the observation of two-year-old specimens of the new variety during May while growing outdoors in containers near West Grove, Pa., U.S.A.

Class: Landscape Shrub Rose.

Plant:

*Height*.—Approximately 27 cm on average when growing in a container.

*Width*.—Approximately 60 cm on average when growing in a container.

*Habit*.—Bushy and rounded.

Branches:

*Color*.—Young stems: near Yellow-Green Group 144A, and smooth in texture. Adult wood: near Greyed-Orange Group 165B overlaid with Greyed-Orange Group 165A, and somewhat rough in texture.

*Thorns*.—Commonly sharply pointed with the tip nearly perpendicular to the stem and pointing downward, approximately 6 in number over a stem length of 21 cm, approximately 6 mm in length on average, approximately 1 mm in width at the base on average, on young stems near Greyed-Yellow Group 161 C overlaid with Greyed-Red Group 182B, and on mature wood near Brown Group 200D.

Leaves:

*Leaves*.—Length: approximately 6 cm on average for a five-leaflet leaf. Width: approximately 5.2 cm on average for a five-leaflet leaf.

*Leaflets*.—Number: 3, 5, and 7. Length: approximately 3.5 cm on average for a terminal leaflet, and approximately 2 cm on average for a lower leaflet. Width: approximately 2 cm on average for a terminal leaflet, and approximately 1.5 cm on average for a lower leaflet. Shape: ovate. Base: obtuse. Margins: serrulate. Texture: smooth on the upper and under surfaces. Overall appearance: attractive dark green with a glossy upper surface. Color (young foliage): Upper surface: commonly Yellow-Green Group 144A, and edged with Greyed-Purple Group 183A. Under surface: commonly Yellow-Green Group 144B. Color (adult foliage): Upper surface: commonly Green Group 137A. Under surface: commonly Green Group 137C.

*Stipules*.—Length: approximately 10 mm on average. Width: approximately 1 mm on average. Color: near Green Group 143C on both surfaces.

*Petioles*.—Length: approximately 2 mm on average. Diameter: approximately 1 mm on average. Color: near Yellow-Green Group 144B.

*Rachis*.—Length: approximately 1.5 mm on average. Diameter: approximately 2 mm on average. Color: near Green Group 143A.

Inflorescence:

*Number of flowers*.—Commonly approximately 27 blooms on average per plant when observed, and commonly in clusters of 5 to 8 blossoms.

*Peduncle*.—Near Yellow-Green Group 144A in coloration, generally smooth in texture with flexible thorns approximately 1 mm in length, relatively short, commonly approximately 1.7 cm in length on average and approximately 3 mm in diameter on average.

*Sepals*.—Upper surface: smooth, covered with short hairs, and commonly near Yellow-Green Group 143C in coloration. Under surface: smooth, covered with short hairs, and near Yellow-Green Group 143A in coloration. Shape: substantially lanceolate. Size: commonly approximately 2.4 cm in length on average, and approximately 0.6 cm in width at the widest point. Margin: entire. Number: five.

*Buds*.—Shape: ovate. Length: approximately 1.5 cm on average as the calyx breaks. Diameter: approximately 1 cm on average as the calyx breaks. Color: when opening Yellow Group 13A blending to Red Group 39B at the apex.

*Flower*.—Form: double. Shape: cup-shaped. Diameter: approximately 5 cm on average when fully open. Depth: approximately 1.3 cm on average. Color (when opening begins): Upper surface: near Yellow Group 13B with Orange Group 31 D at the apex. Under surface: near Yellow Group 9C with Red Group 38C at the apex. Color (at end of blooming): Upper surface: near Yellow-White Group 158D. Under surface: some near White Group 155D. Fragrance: very light sweet scent. Petal number: commonly approximately 23 on average. Petal length: approximately 2.8 cm on average. Petal width: approximately 2.7 cm on average. Petal shape: obovate to obcordate. Petal margin: entire, randomly wavy and recurves with age. Petal apex: obtuse to obcordate. Petal base: narrowly cuneate. Petal texture: glabrous on both surfaces. Lastingness: the flowers commonly last approximately 5 to 7 days on the plant depending on the environmental conditions encountered. Petal drop: good, the petals commonly drop cleanly at full maturity. Stamen: approximately 64 on average. Anthers: near Greyed-Orange Group 169C in coloration. Filaments: approximately 4 mm in length, and near Yellow Group 4C in coloration. Pollen quantity: generally moderate. Pollen color: near Yellow-Orange Group 17A. Pistils: separate and free, and approximately 14 in number on average. Styles: approximately 3 mm in length on average, and near Yellow Group 5C in coloration. Stigmas: approximately 1 mm in diameter on average, and near Yellow Group 6A in coloration. Receptacle: generally oval in shape, smooth in texture, approximately 6 mm in diameter, near Yellow-Green Group 144D in coloration, with achenes standing on the bottom and wall. Hips/seeds: none observed.

Development:

*Vegetation*.—Vigorous and strong.

*Blossoming*.—Abundant and substantially continuous during the growing season.

*Resistance to disease*.—Good, particularly with respect to Black Spot, Powdery Mildew, and Rust.

*Hardiness*.—Has performed well in U.S.D.A. Hardiness Zone No. 5.

I claim:

1. A new and distinct shrub rose plant characterized by the following combination of characteristics:

(a) abundantly and substantially continuously forms in clusters attractive double cup-shaped blossoms that initially are yellow and change to cream-white with maturity, (b) exhibits good petal drop as the blossoms fully mature, (c) exhibits a bushy and rounded growth habit, (d) forms vigorous vegetation, (e) forms attractive dark green foliage having a glossy upper surface that contrasts well with the light blossom coloration, (f) exhibits good resistance to disease, and (g) is well suited for providing attractive ornamentation in the landscape;

substantially as herein shown and described.

* * * * *